United States Patent
Shimose et al.

(10) Patent No.: US 8,188,308 B2
(45) Date of Patent: May 29, 2012

(54) CRYSTAL OF GLUTATHIONE AND PROCESS FOR PRODUCTION THEREOF

(75) Inventors: Tsuyoshi Shimose, Toyonaka (JP); Hideki Murata, Hofu (JP); Tadashi Hayashi, Hofu (JP); Takahiro Sakuma, Hofu (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 160 days.

(21) Appl. No.: 12/445,487

(22) PCT Filed: Oct. 16, 2007

(86) PCT No.: PCT/JP2007/070171
§ 371 (c)(1),
(2), (4) Date: Apr. 14, 2009

(87) PCT Pub. No.: WO2008/047792
PCT Pub. Date: Apr. 24, 2008

(65) Prior Publication Data
US 2010/0099847 A1  Apr. 22, 2010

(30) Foreign Application Priority Data
Oct. 16, 2006  (JP) .................. 2006-281709

(51) Int. Cl.
*C07C 309/00* (2006.01)
*A61K 9/00* (2006.01)

(52) U.S. Cl. .......................... 562/29; 424/400

(58) Field of Classification Search .................. None
See application file for complete search history.

(56) References Cited

U.S. PATENT DOCUMENTS

| | | | |
|---|---|---|---|
| 2,702,799 A | 2/1955 | Laufer et al. | |
| 4,389,331 A * | 6/1983 | Samejima et al. | 427/213.3 |
| 7,078,526 B2 * | 7/2006 | Remenar et al. | 544/336 |
| 7,094,870 B2 | 8/2006 | Shimose et al. | |

FOREIGN PATENT DOCUMENTS

| | | |
|---|---|---|
| EP | 1477409 A1 | 8/2004 |
| JP | 46-43529 B | 12/1971 |
| JP | 51-076483 | 7/1976 |
| JP | 60-105499 | 6/1985 |
| WO | WO-2008/041740 | 4/2008 |

OTHER PUBLICATIONS

Dykstra et al., Excretion, distribution and metabolism of S-(2,4-dinitrophenyl) glutathione in the American cockroach, Insect Biochemistry, vol. 8, Issue 4, 1978, pp. 263-265.*
Merriam-Webster definition of tablet (last viewed on Mar. 7, 2011).*
Merriam-Webster definition of crystal (last viewed on Mar. 7, 2011).*
Cook et al., Results of a controlled clinical trial of glutathione in case of hepatic cirrhosis., Gut, 1965, vol. 6, pp. 472-476.*
Vigneaud et al., The Synthesis of α-Glutamylcysteinylglycine (Isoglutathione), J. Biol. Chem., (1937) vol. 118, pp. 391-395.*
DrugBank: Glutathione (DB00143) (last viewed on Jan. 24, 2012).*
Wright, W.B., The crystal structure of glutathione., Acta Cryst. (1958), vol. 11, pp. 632-642.*
Li et al., "Glutathione: a review on biotechnological production", Appl Microbiol Biotechnol (2004), vol. 66, pp. 233-242.
Qian et al.,"Vibrational Analysis of Glutathione" Biopolymers, vol. 34, No. 10, pp. 1377-1394, (1994).
De Blumenfeld et al., *Journal of Molecular Structure*, 210: 467-475 (1990).
Gorbitz, *Acta Chemica Scandinavica Series B Organic Chemistry and Biochemistry*, 41(5): 362-366 (1987).
European Patent Office, Extended European Search Report in European Patent Application No. 07829905.4 (Dec. 30, 2010).
Japanese Patent Office, International Search Report in International Patent Application No. PCT/JP2007/070171 (Dec. 18, 2007).
Japanese Patent Office, International Written Opinion in International Patent Application No. PCT/JP2007/070171 (Dec. 18, 2007).

* cited by examiner

*Primary Examiner* — Alexander Kim
(74) *Attorney, Agent, or Firm* — Leydig, Voit & Mayer, Ltd.

(57) ABSTRACT

Disclosed is a crystal of glutathione having an average width of 7 to 40 μm and an average particle diameter of 10 to 60 μm, preferably having an angle of repose of 53 degree or less, more preferably having a crude specific volume of 5.0 cm³/g or less, still more preferably in the form of an alpha-form crystal. Also disclosed is a tablet containing such a crystal of glutathione. Further disclosed is a process for producing such a crystal of glutathione.

18 Claims, No Drawings

CRYSTAL OF GLUTATHIONE AND PROCESS FOR PRODUCTION THEREOF

CROSS REFERENCE TO PRIOR RELATED APPLICATIONS

This application is a U.S. national phase application under 35 U.S.C. §371 of International Patent Application No. PCT/JP2007/070171, filed on Oct. 16, 2007, and claims the benefit of Japanese Patent Application No. 2006-281709, filed on Oct. 16, 2006, both of which are incorporated by reference herein. The International Application was published in Japanese on Apr. 24, 2008, as International Publication No. WO 2008/047792 A1 under PCT Article 21(2).

FIELD OF THE INVENTION

The present invention relates to a crystal of glutathione, a tablet containing that crystal and a process for the production of that crystal.

BACKGROUND OF THE INVENTION

Glutathione (gamma-L-glutamyl-L-cysteinyl glycine) is a substance which is present widely in organisms. In addition to being used as a coenzyme, it is known to have a detoxifying action in the liver. Therefore, glutathione is widely used for drugs, health foods and cosmetics as a product, a raw material or an intermediate.

When glutathione is ingested orally, formulations such as tablet, granulations and liquid may be considered. And, liquid preparations are preferable because of ease of ingestion, and tablets are a preferred form because they are superior in portability, easy to dose in a constant amount and can be taken without worrying about taste.

In the manufacture of liquid containing glutathione, there is a need for a glutathione powder with high fluidity and a high solubility in aqueous solutions from the standpoint of handling in manufacturing processes and uniformity of constituents in the liquid preparation.

In the manufacture of tablets containing glutathione, there is a requirement for high fluidity in the glutathione powder used as the raw material from the standpoint of handling in manufacturing processes and uniformity of constituents in the tablet. Particularly when glutathione-rich tablets are manufactured, high compression moldabilities are required along with fluidity. When the fluidity is poor, there are cases where the tablets themselves cannot be manufactured. In addition, when powders with the large particle diameter are used simply to improve the fluidity, there is a possibility that troubles in tableting such as breaking, chipping and capping will arise. In addition, it is commonly known that it is difficult to obtain a tablet having a high level of tablet hardness.

In addition, as glutathione powders, crystalline powders are preferred instead of non-crystalline amorphous from the standpoint of hygroscopic properties, safety and the like. Furthermore, glutathione crystals with a small specific volume are desirable from the standpoint of easy transportation and costs.

Fermentation methods using microorganisms such as yeast and enzymatic methods (Applied Microbiology and Biotechnology, 66, 233 (2004)) are known as manufacturing methods for glutathione. Glutathione crystals acquired from a culture or reaction mixture that contains glutathione and is obtained by these methods are on the market, but there are difficulties in terms of fluidity, packing properties, tabletability, ease of dissolution and the like. There is a need for glutathione crystals with improvements to these points, but glutathione crystals with superior fluidity, packing properties, tabletability and ease of dissolution and a process for producing these crystals are not known.

SUMMARY OF THE INVENTION

It is an object of the present invention to provide glutathione crystals with superior fluidity, packing properties, tabletability and ease of dissolution and a process for production thereof.

The present invention relates to glutathione crystals having an average width of 7 to 40 μm and an average particle diameter of 10 to 60 μm.

The present invention also relates to the glutathione crystals above wherein the angle of repose is 53° or less.

The present invention further relates to the glutathione crystals above wherein the crude specific volume is 5.0 cm³/g or less.

The present invention further relates to any one of the crystals above wherein the glutathione crystals are alpha-form crystals.

The present invention further relates to a tablet containing any one of the glutathione crystals above.

The present invention further relates to a process for producing any one of the glutathione crystals above which includes agitating for five hours or more, allowing the glutathione to be crystallized in the aqueous solution and recovering the glutathione crystals from that aqueous solution after glutathione crystals are added as seed crystals to an aqueous solution in which glutathione is dissolved.

According to the present invention, there are provided glutathione crystals with superior fluidity, packing properties, tabletability and ease of dissolution, a tablet containing those crystals and a process for producing those crystals.

DETAILED DESCRIPTION OF THE INVENTION

1. Glutathione Crystals of the Present Invention

The shape of a crystal may be expressed by ratio (L/D) of the "length" (L) of the vertical direction of the crystal and the "width" (D) in the horizontal direction. Even if crystals have the same L/D, the significance of the width of a columnar crystal is more significant when a needle-like crystal is compared to a columnar crystal.

Crystals where the average width is 7 to 40 μm, preferably 15 to 40 μm, more preferably 20 to 40 μm and even more preferably 25 to 30 μm and the average particle diameter is 10 to 60 μm, preferably 20 to 60 μm, more preferably 30 to 60 μm and even more preferably 40 to 55 μm may be cited for the glutathione crystals of the present invention.

Glutathione crystals where the average width is less than 7 μm, particularly 5 μm or less, and the average particle diameter is less than 10 μm have poor fluidity, and when glutathione-rich tablets, for example tablets containing 30% by weight or more are compression molded using tableting machines, there are troubles such as tableting not being possible because the crystals are not packed uniformly into the mortar.

In addition, crystals with an average width of 7 to 40 μm and an average particle diameter of 10 to 60 μm and further an angle of repose of 53° or less, preferably 52° or less, more preferably 51° or less and even more preferably 50° or less may be cited for the glutathione crystals of the present invention. Glutathione crystals with an angle of repose that is larger than 53° cannot be completely ejected from the bottom of the hopper unless the angle of inclination of the bottom of the hopper is greater than 53° when they are discharged, so the device is limiting, and handling is complicated.

Furthermore, crystals with an average width of 7 to 40 μm and an average particle diameter of 10 to 60 μm and in addition a crude specific volume of 5.0 cm$^3$/g or less, preferably 2.0 to 5.0 cm$^3$/g and more preferably 3.0 to 5.0 cm$^3$/g may be cited for the glutathione crystals of the present invention. Since crystals with a crude specific volume of 5.0 cm$^3$/g or less have superior packing properties, handling is easier in various processes than with crystals that have a specific volume greater than 5.0 cm$^3$/g. In addition, costs are lower for transportation.

Furthermore, crystals with an average width of 7 to 40 μm and an average particle diameter of 10 to 60 μm and in addition superior solubility in water may be cited for the glutathione crystals of the present invention.

Glutathione crystals where the time from putting 12 g of the glutathione crystals into 200 ml deionized water maintained at a temperature of 37° C. and agitated at 120 rpm until the crystals completely dissolve is 100 seconds or less, preferably 80 seconds or less, more preferably 70 seconds or less, even more preferably 68 seconds or less and particularly preferably 65 seconds or less may be cited as crystals with superior solubility in water.

The glutathione crystals of the present invention may be crystalline powders that contain crystal polymorphs such as form alpha and form beta, but alpha-form crystals are preferable for the glutathione crystals. Crystalline powders where the proportion of alpha-form crystals in the total glutathione is 95% or more, preferably 97% or more, more preferably 98% or more, even more preferably 99% or more, particularly preferably 99.5% or more and most preferably 99.9% or more may be cited for the crystalline powder.

2. Tablet Containing Glutathione of the Present Invention

Tablets obtained by mixing of powders such as the glutathione crystals of the present invention described above, diluting agents and lubricants and then molding such as compression molding may be cited for the tablet which contains the glutathione crystals of the present invention.

The tablet of the present invention is a conventional tablet, coated tablet, sustained-release tablet, tablet that quickly releases in the oral cavity, buccal tablet, chewable tablet or the like and has the glutathione crystals of the present invention as the principal ingredient. Otherwise, it may contain normal diluting agents, disintegrating agents and the like that are used in normal nutritional foods or drugs. In addition, it may further contain binders, lubricants and other additives as needed. The proportion of glutathione in the tablet is preferably approximately 10 to 95% by weight, more preferably approximately 20 to 80% by weight and even more preferably approximately 30 to 60% by weight.

For example, sugars (monosaccharides, disaccharides and polysaccharides), sugar alcohols and the like may be cited, and preferably monosaccharides, disaccharides and sugar alcohols may be cited for the diluting agent. The proportion of diluting agents in the tablet is preferably approximately 10 to 90% by weight, more preferably approximately 15 to 60% by weight and even more preferably approximately 20 to 40% by weight.

For example, lactose, sucrose, maltose, trehalose and the like may be cited for the monosaccharides and disaccharides. For example, mannitol, reduced maltose syrup, reduced palatinose, maltitol, maltol, lactitol, xylitol, sorbitol, erythritol and the like may be cited for the sugar alcohols. The monosaccharides, disaccharides or sugar alcohols are selected from any one or a combination of two or more according to the oxidized glutathione content.

In addition, beta-cyclodextrin, crystalline cellulose and the like may be cited for polysaccharide diluting agents, and beta-cyclodextrin is particularly preferable in a form of tablet that quickly releases in the oral cavity.

For example, cornstarch, white potato starch, carboxymethylcellulose, calcium carboxymethylcellulose, sodium carboxymethylcellulose, crospovidone, croscarmellose sodium, sodium starch glycolate and the like may be cited for disintegrating agents, and preferably calcium carboxymethylcellulose or sodium starch glycolate may be cited. The proportion of disintegrating agent in the tablet is preferably 0.5 to 20% by weight, more preferably 0.5 to 5% by weight, and even more preferably 0.5 to 2% by weight.

For example, methylcellulose, ethyl cellulose, carboxymethylcellulose, polyvinylpyrrolidone, pullulan, acrylate polymers, polyvinyl alcohol, gelatin, agar, gum arabic, gum arabic powder, xanthan gum, tragacanth, guar gum, gellan gum, locust bean gum, partial alpha-starch, macrogol and the like may be cited for binders. The proportion of binder in the tablet is preferably 0.5 to 5% by weight, more preferably 0.5 to 3% by weight and even more preferably 0.5 to 2% by weight.

For example, sucrose fatty acid esters, glycerin fatty acid esters, magnesium stearate, calcium stearate, sodium stearyl fumarate, talc, sodium lauryl sulfate, light anhydrous silicic acid, hydrated silicon dioxide and the like may be cited for lubricants. The proportion of lubricant in the tablet is preferably 0.05 to 10% by weight, more preferably 0.1 to 5% by weight and even more preferably 0.1 to 3% by weight.

Beta-carotene, yellow food coloring no. 5, red food coloring no. 2, green food coloring no. 2 and other food colorants, food grade lake colorants, red iron oxide, niacin and other colorants, vitamin E, ascorbic acid, vitamin Bs, vitamin A, vitamin D or derivatives of these and other vitamins, sodium and other minerals, aspartame, glucose, fructose, sucrose, stevia, saccharose, saccharine sodium, thaumatin, acesulfame potassium and other sweeteners, silicate dioxide, calcium silicate, synthetic aluminum silicate, talc, calcium hydrogen phosphate and other anticaking agents, baking soda and other foaming agents, citric acid, malic acid, tartaric acid and other acidulants, lemon flavor, lemon lime flavor, orange flavor, grapefruit flavor, menthol and other flavoring ingredients may be cited for the other additives, and among these one or two or more may be used as needed. The proportion of other additives in the tablet is preferably 0.01 to 5% by weight, more preferably 0.1 to 3% by weight and even more preferably 0.1 to 1% by weight.

The composition including glutathione crystals of the present invention, diluting agents and lubricants and the like can be processed into the tablet by either direct compression molding or tableting by a wet method. For example, a method where the glutathione crystals of the present invention and powders of a diluting agent, lubricant and the like are mixed as uniformly as possible, fed directly into a tableting machine and tableted may be cited for the process for the tablet.

The hardness of the tablet of the present invention is 3 to 20 kgf, preferably 4 to 15 kgf. The normal diameter for the size of a single tablet is preferably 5 to 20 mm, and the weight thereof is preferably 200 to 2000 mg. In addition, the shape of the tablet described above is various, such as round, square, hexagonal, round cylindrical and the like and is not limited in particular.

3. Process for Producing Glutathione Crystals of the Present Invention

The process for producing the glutathione crystals of the present invention is a process where, after glutathione crystals are added as seed crystals to an aqueous solution in which glutathione is dissolved, there is agitation for five hours or more, the glutathione in the aqueous solution is crystallized and the crystals of glutathione are recovered from the aqueous solution.

Solutions from which impurities have been eliminated and the like, such as solutions containing glutathione obtained by publicly known glutathione producing processes, for example cultures that contain glutathione obtained by culturing microorganisms that have the ability of producing glutathione, reaction solutions that contain glutathione obtained by enzymatic methods (Applied Microbiology and Biotechnology, 66, 233 (2004), Published Unexamined Patent Application No. S60-105499 and the like) and the like may be cited for the aqueous solution in which glutathione is dissolved.

*Candida Krusei* IFO 011 (Published Unexamined Patent Application No. S60-160894), *Saccharomyce scerevisiae* IFO 2044 (Published Unexamined Patent Application No. S54-138190), *Escherichia coli* ATCC 11303 (Published Unexamined Patent Application No. S60-105499), *Corynebacterium glutamicum* ATCC 21171 (Published Unexamined Patent Application No. S60-27397), *Proteus mirabilis* IFO 3849 (Published Unexamined Patent Application No. S57-2698) and the like, as well as microorganisms genetically transformed by DNA (gshA) encoding gamma-glutamyl-cysteine synthetase (GSHI) and DNA (gshB) encoding glutathione synthetase (GSHII) may be cited for the microorganisms having the ability to produce glutathione used in enzymatic methods. *E. coli* RC912/pBR322-gshII (FERM BP-366) and *E. coli* RC912/pBR325-gshI/II (FERM BP-337) and the like, which contain gshA or gshB and are derived from *Escherichia coli* as recited in Published Unexamined Patent Application No. H02-31690 may be cited for genetically transformed strains as in the above.

The culture containing the glutathione can be obtained by culturing the microorganisms above in a medium and allowing the glutathione to be formed and accumulated in the culture.

The medium for culturing the microorganisms having the ability of producing glutathione may be either a synthetic medium or natural medium as long as it contains the nutrients necessary for breeding the microorganisms of the present invention and synthesizing amino acids such as a carbon source, nitrogen source, mineral salts, vitamins and the like.

The carbon source may be any carbon source that can be utilized by the microorganism, and sugars such as glucose and fructose, alcohols such as ethanol and glycerol, organic acids such as acetic acid and the like may be cited.

Ammonia, ammonium sulfate and other ammonium salts, amines and other nitrogen compounds, peptone, soybean hydrolysate and other natural sources of nitrogen and the like may be cited for the nitrogen source.

Potassium phosphate, magnesium sulfate, sodium chloride, ferrous sulfate, potassium carbonate and the like may be cited for the mineral salts.

Biotin, thiamine and the like may be cited for the vitamins. Furthermore, substances necessary for the growth of the microorganisms that have the capability of producing glutathione may be added if needed.

The culture is preferably carried out under aerated conditions such as a shaking culture or aerated agitation culturing. The culturing temperature is 20 to 50° C., preferably 20 to 42° C. and more preferably 28 to 38° C. The pH for the culturing is 5 to 9, preferably 6 to 7.5. The culturing time is five hours to five days, preferably 16 hours to three days.

During culturing or afterwards, the culture itself may be used as the enzyme source in enzymatic process for producing glutathione. And, microbial cells separated from the culture by centrifugation or a membrane filtration or microbial cells which maintain the microbial form and have substantially the same activity as the microbial cells before the treatments such as the microbial cells obtained by washing the microbial cells, drying the microbial cells, freezing the microbial cells, freeze-drying the microbial cells, treating the microbial cells with surfactant, treating the microbial cells with organic solvent or treating the microbial cells with enzymes or the like may be used as an enzyme source in the same manner.

Polyethylene glycol stearylamine (for example, Nymeen S-215, NOF Corporation), alkyl dimethyl benzyl ammonium chloride (for example, Sanizol B-50, Kao Corporation) and other cationic surfactants, sodium lauryl sulfate (for example, PERSOFT® SL, NOF Corporation) and other anionic surfactants, polyethylene glycol sorbitan monostearate (for example, Nonion ST221, NOF Corporation) and other nonionic surfactants, dimethyl lauryl betaine (for example, Nissan Anon BL, NOF Corporation) and other ampholytic surfactants and the like may be cited for surfactants. Normally, 0.1 to 20 g/l of these are used, preferably 1 to 10 g/l.

Toluene, xylene, aliphatic alcohols, acetone, ethyl acetate and the like may be cited for organic solvents, and normally 0.1 to 50 ml/l of these are used, preferably 1 to 20 ml/l.

Using the culture described above, microbial cells obtained from the culture or treated microbial cells of the microbial cells as enzyme source, and allowing L-glutamic acid, L-cysteine or L-cystine and glycine to be present in an aqueous medium, glutathione is formed and accumulated in the medium. As necessary, ATP or energy donors, phosphate ions, magnesium ions and the like ingredients necessary for producing ATP from ADP using the activity of the enzyme source described above may be made present in the medium.

ATP may be used in a concentration of 0.5 to 200 mmol/l.

There are no limits for the energy donors as long as they are substances that are utilized by the enzyme source described above and cause the production of ATP, and glucose, arabinose, lactose, maltose, sucrose, mannitol, sorbitol, trehalose, molasses, starch resolvents and other carbohydrates, pyruvic acid, lactic acid, acetic acid, alpha-ketoglutaric acid and other organic acids, glutamic acid and other amino acids and the like may be used for this substance. These are used in a concentration of 1 to 200 g/l.

The concentration of phosphate ions and magnesium ions in the aqueous medium is preferably maintained in a range of 4 to 400 mmol/l. Sodium salts, potassium salts, magnesium salts and the like of phosphoric acid may be used as the phosphate ions. Either magnesium chloride and other inorganic salts or magnesium phosphate and other organic salts may be used as the magnesium ions.

L-cysteine and L-cystine may be used alone or mixed. L-glutamic acid, L-cysteine or L-cystine and glycerin are used in a concentration of 1 to 300 mmol/l each.

Any medium is suitable for the aqueous medium as long as it does not inhibit the production reaction for glutathione, and for example, water, phosphate buffer solutions, tris buffer solutions, boric acid buffer solutions and the like may be cited. In addition, the supernatant of the culture obtained by culturing the transformant may be used as it is for the aqueous medium. In addition, a surfactant or organic solvent may be added to the aqueous medium described above as necessary. The production efficiency for glutathione may be increased by adding a surfactant or organic solvent. The types and concentrations of surfactants and organic solvents are the same as for treating the microbial cells described above.

The reaction for producing glutathione is carried out at a temperature of 10 to 70° C., preferably 20 to 40° C., pH adjusted to a range of 4 to 10, preferably 6 to 9 for 1 to 48 hours, preferably 2 to 24 hours. Adjustment of pH is carried out using an inorganic or organic acid, alkali solution, urea, calcium carbonate, ammonia or the like.

After completion of the glutathione producing reaction, the glutathione in the reaction mixture may be reduced by keeping the reaction mixture as is without aeration or agitation for 1 to 20 hours, preferably 5 to 17 hours and more preferably 8 to 15 hours.

Culture containing glutathione may be obtained by centrifugation or a membrane filtration on the culture that contains the glutathione obtained by the method described above.

After the completion of the reaction, precipitates are eliminated by centrifugation or a membrane filtration on the reaction mixture. A copper salt complex of glutathione is obtained by adding copper oxide to the reaction mixture obtained. After washing this copper salt complex and eliminating the copper by hydrogen sulfide, activated carbon decolorization is carried out, and a glutathione containing solution, which contains glutathione at a concentration of 500 to 700 g/l may be obtained by vacuum concentration.

Glutathione crystals are added as seed crystals to the solution in which the glutathione is dissolved. The amount of seed crystals to be added is 10 to 500 mg/l, preferably 20 to 200 mg/l and more preferably 30 to 100 mg/l. After the seed crystals are added, agitation is carried out at 0 to 45° C., preferably 0 to 40° C. and more preferably 10 to 35° C. for 5 to 30 hours, preferably 10 to 25 hours and more preferably 15 to 20 hours.

Subsequently, a crystal slurry can be obtained by cooling down to 0 to 30° C., preferably 0 to 25° C. and more preferably 0 to 20° C. and further keeping agitating another 30 minutes to 10 hours, preferably 1 to 8 hours and more preferably 2 to 5 hours after an equal volume of 50 to 70% v/v conc. aqueous solution of water-miscible organic solvent, such as methanol, ethanol and acetone, preferably an aqueous solution of ethanol, is added to this glutathione solution in 1 to 10 hours, preferably 2 to 8 hours and more preferably 3 to 6 hours at 0 to 45° C., preferably 0 to 40° C. and more preferably 10 to 35° C.

After this crystal slurry is cooled to 0 to 15° C., preferably 0 to 13° C. and more preferably 0 to 10° C., the crystals are separated using a basket centrifuge. The glutathione crystals of the present invention are obtained by drying for 1 to 48 hours, preferably 5 to 36 hours and more preferably 10 to 30 hours in a dryer at 30 to 50° C., preferably 35 to 45° C.

By controlling the agitation time after the seed crystals are added, and the time of addition and temperature of the organic solvent within the ranges described above, it is possible to prepare the desired glutathione crystals with an average width of 7 to 40 μm and an average particle diameter in the range of 10 to 60 μm.

In addition, glutathione crystals of the present invention which have a smaller average width and average particle diameter than crystals obtained by crystallization may be obtained by crushing of the glutathione crystals obtained by the method described above using commercially available crusher, a mortar and the like. Glutathione crystals of the present invention having a desired average width and average particle diameter are obtained by adjusting the speed of rotation, crushing speed and size of sieves when a crusher is used and adjusting the grinding time when a mortar is used.

Moreover, the average width, average particle diameter, angle of repose and crude specific volume of the crystals are measured as follows in the present specification.

(1) Average Width

The crystals were observed and photographed using a VH-8000 digital microscope (Keyence Corporation). The width of approximately 300 crystals was measured and calculations performed.

(2) Average Particle Diameter

This is synonymous with volume median diameter, and it was measured using a laser diffraction and scattering particle diameter analyzer, the LMS-24 SK Laser Micron Sizer (Seishin Enterprise Co. Ltd.) and expressed as a cumulative 50% volume particle diameter.

(3) Angle of Repose

This was measured using a three-wheel cylindrical rotating angle of repose measuring device and is expressed by the average value for three measurements.

(4) Crude Specific Volume

This is expressed as the reciprocal of a bulk density measurement made based on the Japanese Pharmacopoeia.

EXAMPLE 1

Glutathione Crystal Production 1

*E. coli* RC912/pBR325-gshI/II (FERM BP-337) that is used in the following method is available from the National Institute of Advanced Industrial Science and Technology International Patent Organism Depositary.

In addition, *E. coli* RC912/pBR325-gshI/II may be constructed by the following method. That is, a mutant strain (*E. coli* RC912) where the inhibition of the gamma-glutamyl-cysteine synthetase is eliminated is prepared according to methods described in Published Unexamined Patent Application No. S58-20196 (U.S. Pat. No. 4,596,775) and the Journal of General Microbiology, 128, 1047-1052 (1982). *E. coli* RC912 is also available from the International Patent Organism Depositary as FREM BP-47.

Next, a PstI digested fragment that contains the gamma-glutamyl cysteine synthetase structural gene on the chromosome of *Escherichia coli* RC912 strain is cloned on a plasmid pBR322 according to the method described in Published Unexamined Patent Application No. H02-31690 (EP 107400) and Applied and Environmental Microbiology, 44, 1444-1448 (1982). Furthermore, a Hind III digested fragment that contains the glutathione synthetase structural gene on the chromosome of *E. coli* RC912 strain is cloned on a plasmid pBR322 according to the method described in Published Unexamined Patent Application No. H02-31690 and Agricultural and Biological Chemistry, 47, 1381-1383 (1983). In addition, these two cloned fragments are introduced onto a single vector plasmid pBR325 according to the method described in Published Unexamined Patent Application No. H02-31690 and Bioprocess Technology, 19, 159-183 (1994), and the pBR325-gshI/II described in Published Unexamined Patent Application No. H02-31690 and Bioprocess Technology 19, 159-183 (1994) can be prepared.

*E. coli* RC912/pBR325-gshI/II (FERM BP-337) was inoculated into 10 ml seed medium (1 g/l glucose, 10 g/l bacto tryptone, 5 g/l yeast extract, 5 g/l sodium chloride, adjusted to the pH of 7.2), cultured for 16 hours at 30° C. and the obtained culture further inoculated into a 300 ml seed medium and cultured for 8 hours at 30° C.

The obtained culture was added to a 10 L main medium (10 g/l glucose, 10 g/l peptone, 10 g/l yeast extract, 5 g/l meat extract, 1 g/l magnesium sulfate septahydrate and 5 g/l potassium dihydrogen phosphate, adjusted to a pH of 7.0). The culture was done at 28° C. and 600 rpm, with aeration conditions of 10 L/min for 30 hours.

Various constituents were added to make this culture have 900 g/l glucose, 1 g/l disodium hydrogen phosphate, 5 g/l magnesium sulfate septahydrate, 1.5 g/l phytic acid, 3.5 g/l potassium sulfate, 8 g/l Nymeen S-215 (NOF Corporation), 10 ml/l xylene, 25 mmo/l sodium glutamate, 25 mmo/l glycine and 25 mmo/l L-cystine. The pH was adjusted to 7.2, and the reaction was carried out at 34° C. and 600 rpm with aeration conditions of 10 L/min for 7 hours. Subsequently, it was held for 13 hours in a non-aerated, non-agitated state to reduce the glutathione in the reaction solution.

After the precipitate was eliminated from the reaction mixture by centrifugation, copper oxide was added and a glutathione copper complex was obtained. After washing this copper complex and removing the copper with hydrogen sulfide, activated carbon decolorization was carried out and a glutathione solution which includes glutathione in a concentration of 600 g/l was obtained.

Next, 0.005 g of glutathione crystals (Kohjin Co., Ltd.) were added to this glutathione solution as seed crystals and the solution was agitated for 15 hours at 25° C. Subsequently, after an equal volume of 58% v/v conc. ethanol solution to the glutathione solution was added to the solution in 4 hours at 25° C., the solution was cooled down to 15° C. The solution was further agitated for 3 hours, and the crystal slurry was obtained.

After this crystal slurry was cooled to 10° C., it was separated in a basket centrifuge, and glutathione crystals (alpha-form crystals) with an average width of 25 μm and an average particle diameter of 52 μm were obtained by drying for 24 hours at 40° C. in a vacuum drying oven.

EXAMPLE 2

Glutathione Crystal Production 2

The glutathione crystals obtained in Example 1 were ground using a mortar and pestle. The operation was continued measuring the average width and average particle diameter of the crystals as needed, and glutathione crystals with an average width of 14 μm and an average particle diameter of 26 μm and glutathione crystals with an average width of 7 μm and an average particle diameter of 11 μm were obtained.

EXAMPLE 3

Production of Tablet Containing Glutathione

The glutathione crystals obtained in Example 1 and 2 and reduced palatinose (Mitsui Sugar Co., Ltd.) and sucrose fatty acid ester (Daiichi Kagaku Kogyo Co., Ltd.) were mixed in the proportions in Table 1 and were sufficiently mixed in a polyethylene bag. The mixed powder was directly compression molded using a single punch tableting machine (6B-2M rigid type molding machine, Kikusui Seisakusho, Ltd.), and a 300 mg tablet with a diameter of 9 mm produced. The tableting pressure was set at 764 kg. The hardness of the tablet was measured using a KHT-20N hardness testing machine (Fujiwara Scientific Co.). No tableting failure was found, and a tablet with sufficient tablet hardness values was obtained.

TABLE 1

| | | Average width of raw material glutathione crystals (μm) | | | |
| | | 25 | 25 | 14 | 7 |
| | | Average particle diameter of raw material glutathione crystals (μm) | | | |
| | Raw material | 52 Blending Example 1 Mixture (% by weight) | 52 Blending Example 2 Mixture (% by weight) | 26 Blending Example 3 Mixture (% by weight) | 11 Blending Example 4 Mixture (% by weight) |
|---|---|---|---|---|---|
| Formula | Glutathione | 20 | 30 | 30 | 30 |
| | Reduced palatinose | 75 | 65 | 65 | 65 |
| | Sugar ester | 5 | 5 | 5 | 5 |
| Tableting | Tableting pressure (kg) | 1,193 | 1,183 | 1,191 | 1,213 |
| | Tablet weight (mg) | 316 | 309 | 311 | 298 |
| | Tablet hardness (kgf) | 5.7 | 4.6 | 6.8 | 4.9 |

COMPARATIVE EXAMPLE 1

The average width, average particle diameter, angle of repose and crude specific volume of the glutathione crystals obtained in Examples 1 and 2 were compared with commercially available glutathione (commercial product A) crystals (Table 2).

TABLE 2

| Sample | Example 1 | Example 2 | | Commercial product A |
|---|---|---|---|---|
| Average width (μm) | 25 | 14 | 7 | 3 |
| Average particle diameter (μm) | 52 | 26 | 11 | 9 |
| Angle of repose (degrees) | 48 | 51 | 52 | 56 |
| Crude specific volume (cm³/g) | 3.3 | 2.7 | 3.3 | 8.2 |

While the glutathione crystals obtained in Examples 1 and 2 were columnar, commercial product A was needle-like crystals. In addition, when the average width was measured for crystals of commercial products B and C, both were 3 μm, and they were needle-like crystals as commercial product A and had dry and fluffy physical properties.

COMPARATIVE EXAMPLE 2

Production of a tablet containing glutathione was tried by the same method as in Example 2 using commercially available glutathione crystals (commercial product A). The results are shown in Table 3.

TABLE 3

| | Raw material | Blending Example 1 Mixture (% by weight) | Blending Example 2 Mixture (% by weight) |
|---|---|---|---|
| | Average width of raw material glutathione crystals (μm) | 3 | |
| | Average particle diameter of raw material glutathione crystals (μm) | 9 | |
| Formula | Glutathione | 20 | 30 |
| | Reduced palatinose | 75 | 65 |
| | Sugar ester | 5 | 5 |
| Tableting | Tableting pressure (kg) | 1,173 | Impossible to tablet |
| | Tablet weight (mg) | 302 | |
| | Tablet hardness (kgf) | 6.0 | |

When the glutathione crystals of the present invention were used, it was possible to mold a tablet containing 30% glutathione as shown in Example 3, but when commercial product A was used, the raw materials were not uniformly packed into the mortar of the tableting machine, so it was not possible to produce the tablet itself.

COMPARATIVE EXAMPLE 3

The solubility of the glutathione crystals obtained in Example 1 and commercially available glutathione crystals (commercial product A) was compared by the following method.

12 g of each of the crystals was put in to 200 ml of the ionized water maintained at a temperature of 37° C., and the time from injection to complete dissolution of the crystals when agitated at 120 rpm was measured. The results are shown in Table 4.

TABLE 4

| Sample | Example 1 | Commercial product A |
|---|---|---|
| Dissolution time (seconds) | 65 | 124 |

As is shown in Table 4, it was found that the solubility of the glutathione crystals of the present invention was better than that of commercial product A.

The crystals of the present invention are superior in fluidity, packing properties, tabletability and ease of dissolution and are industrially useful.

The invention claimed is:

1. Glutathione crystals having an average width of 7 to 40 μm and an average particle diameter of 10 to 60 μm, wherein the glutathione is gamma-L-glutamyl-L-cysteinyl glycine.

2. The glutathione crystals according to claim 1, wherein the angle of repose is 53° or less.

3. The glutathione crystals according to claim 2, wherein the glutathione crystals are alpha-form crystals.

4. The glutathione crystals according to claim 1, wherein the crude specific volume is 5.0 cm$^3$/g or less.

5. The glutathione crystals according to claim 4, wherein the glutathione crystals are alpha-form crystals.

6. The glutathione crystals according to claim 1, wherein the glutathione crystals are alpha-form crystals.

7. The glutathione crystals according to claim 2, wherein the crude specific volume is 5.0 cm$^3$/g or less.

8. A tablet comprising the glutathione crystals according to claim 1.

9. A tablet comprising the glutathione crystals according to claim 2.

10. A tablet comprising the glutathione crystals according to claim 4.

11. A tablet comprising the glutathione crystals according to claim 6.

12. A process for producing the glutathione crystals according to claim 1, the process comprising the steps of: adding glutathione crystals as seed crystals to an aqueous solution in which glutathione is dissolved; agitating said aqueous solution for five hours or more; allowing the glutathione to be crystallized in said aqueous solution; and recovering the glutathione crystals of claim 1 from said aqueous solution.

13. A process for producing the glutathione crystals according to claim 2, the process comprising the steps of: adding glutathione crystals as seed crystals to an aqueous solution in which glutathione is dissolved; agitating said aqueous solution for five hours or more; allowing the glutathione to be crystallized in said aqueous solution; and recovering the glutathione crystals of claim 2 from said aqueous solution.

14. A process for producing the glutathione crystals according to claim 3, the process comprising the steps of: adding glutathione crystals as seed crystals to an aqueous solution in which glutathione is dissolved; agitating said aqueous solution for five hours or more; allowing the glutathione to be crystallized in said aqueous solution; and recovering the glutathione crystals of claim 3 from said aqueous solution.

15. A process for producing the glutathione crystals according to claim 4, the process comprising the steps of: adding glutathione crystals as seed crystals to an aqueous solution in which glutathione is dissolved; agitating said aqueous solution for five hours or more; allowing the glutathione to be crystallized in said aqueous solution; and recovering the glutathione crystals of claim 4 from said aqueous solution.

16. A process for producing the glutathione crystals according to claim 7, the process comprising the steps of:
    adding glutathione crystals as seed crystals to an aqueous solution in which glutathione is dissolved;
    agitating said aqueous solution for five hours or more;
    allowing the glutathione to be crystallized in said aqueous solution; and
    recovering the glutathione crystals of claim 7 from said aqueous solution.

17. A process for producing the glutathione crystals according to claim 3, the process comprising the steps of:
    adding glutathione crystals as seed crystals to an aqueous solution in which glutathione is dissolved;
    agitating said aqueous solution for five hours or more;
    allowing the glutathione to be crystallized in said aqueous solution; and
    recovering the glutathione crystals of claim 3 from said aqueous solution.

18. A process for producing the glutathione crystals according to claim 5, the process comprising the steps of:
    adding glutathione crystals as seed crystals to an aqueous solution in which glutathione is dissolved;
    agitating said aqueous solution for five hours or more;
    allowing the glutathione to be crystallized in said aqueous solution; and
    recovering the glutathione crystals of claim 5 from said aqueous solution.

* * * * *